United States Patent [19]

Ivanova et al.

[11] Patent Number: 4,806,548

[45] Date of Patent: Feb. 21, 1989

[54] ANTI-ULCER COMPOSITION

[75] Inventors: Nedyalka S. Ivanova; Tshavdar B. Ivanov; Margarita D. Dryanska; Orhideya B. Zabunova; Lilyana D. Dalleva; Milka P. Nikolova; Nikolina D. Berova; Rossitza S. Rakovska; Maria S. Stoyanova; Sascha R. Mihaylova; Milka A. Luna; Jossif N. Nissimou; Snejana G. Vitkova; Vladimir K. Matov; Boris K. Dimitrov; Grigor M. Metshkov, all of Sofia, Bulgaria

[73] Assignee: T P O Pharmachim, Sofia, Bulgaria

[21] Appl. No.: 81,496

[22] Filed: Aug. 4, 1987

Related U.S. Application Data

[63] Continuation-in-part of Ser. No. 722,313, Apr. 11, 1985.

[30] Foreign Application Priority Data

Apr. 13, 1984 [BG] Bulgaria .................................. 65090

[51] Int. Cl.$^4$ .............................................. A61K 31/47
[52] U.S. Cl. .................................... 514/310; 514/400; 514/925
[58] Field of Search ............... 514/310, 400, 925, 926; 546/143

[56] References Cited

U.S. PATENT DOCUMENTS 3,577,424  5/1971  Ehrhart et al. ..................... 564/182

FOREIGN PATENT DOCUMENTS 0056465  4/1982  Japan ................................... 514/400

*Primary Examiner*—Paul Lieberman
*Assistant Examiner*—Christine A. Skane
*Attorney, Agent, or Firm*—Klein & Vibber

[57] ABSTRACT

This invention relates to an improved anti-ulcer composition for prophylaxis and treatment of stomach and duodenum ulcers, including stress ulcers. The composition provides potent anti-ulcer activity with a dramatic reduction in toxicity and harmful side effects. The composition comprises a histamine $H_2$ antagonist based on a guanidine derivative, preferably [N-cyano-H'-methyl-N"]-2(4-methyl-imidazolyl)-methylthio-[ethylguanidine]; and at least one 4-phenyl-tetrahydroisoquinoline antidepressant, preferably the [+] isomer of 4-phenyl-2-methyl-8-amino-1,2,3,4-tetrahydroisoquinoline hydrogen maleate. The composition may also contain a spasmolytic agent, preferably 2-metoxycarbonyl-4-(beta-piperidino ethyl) -metoxycarbonyl-4-(beta-peperidino-ethyl) benzophenone. The ratio of antagonist to antidepressant ranges from 2:1 to 60:1, and the ratio of their sum to the spasmolytic agent, when used, ranges from 2.2:1 to 42.5:1.

9 Claims, No Drawings

ANTI-ULCER COMPOSITION

This is a continuation-in-part of Ser. No. 722,313, filed Apr. 11, 1985.

This invention relates to an anti-ulcer composition for prophylasis and treatment of stomach and duodenum ulcers, including stress ulcers, such as those caused by severe trauma or shock, caused, for example, by burns, freezing, surgical intervention, or internal disease.

BACKGROUND OF THE INVENTION

Antagonists of histamine H$_2$-receptors are known to inhibit the stomach secretions of humans and animals. The known antagonists include guanidine derivatives, such as:

[N-cyano-N'-methyl-N"]-2(4-methyl-imidazolyl)-methylthio[ethylguanidine] ("cimetidine"), U.S. Pat. No. 3,950,353; and ranitidine-[N-[2]-(5-dimethylaminomethyl-2-furanyl)-methyl]thioethyl-[N-methyl-2-nitro-1,1-ethenediamine], Great Britain Pat. No. 1,565,966.

These antagonists are effective in suppressing histamine and pentagastrin stimulated secretions. There are, however, serious disadvantages and side effects related to their use. Cimetidine, for example, may cause or exacerbate erosion of the stomach-duodenal mucous membranes, stomach cancer, perforation, pancreatitis, bradicardia, leucopenia, agranulocitoma, dermic hypersensitivity, autoimmunic hemolytic hepatitis, hypereglycemia, and muscle pains. H. Kato et al, *Arch. Pharmacol. et Therapie*, 249(2), pp. 247–56 (1981).

Other known compounds include 4-phenyltetrahydroisoquinolines of the formula I:

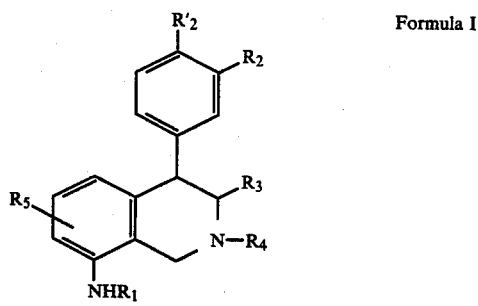

Formula I wherein R$_1$, R$_3$, and R$_4$ are each a hydrogen, a lower alkyl, or an aralkyl group; R$_2$ and R'$_2$ are each a hydrogen, a halogen atom, a trifluormethyl group, an alkyl, alkoxy, or aralkoxy group; and R$_5$ is a hydrogen or halogen atom, a hydroxylic, trifluormethyl, or nitro group, or a lower alkyl, alkoxy, or aralkoxy group. These compounds are antidepressants, a well-known species of which is 4-phenyl-2-methyl-8-amino-1,2,3,4-tetrahydroisoquinoline hydrogen maleate ("nomiphenzene"). Great Britain Pat. No. 1,670,694.

Another known compound is 2-metoxycarbonyl-4-(betapiperidinoethyl)benzophenone hydrochloride ("baralginketone"), which has a spasmolytic and analgesic effect. C.A. 50, 9623c, E. Lindner, Arzn. Forsch., 6, pp. 124–7 (1956).

SUMMARY OF THE INVENTION

The object of this invention is to provide an anti-ulceric composition with potent and reinforced anti-ulceric activity that is also minimally toxic and that expresses only weak side-effects.

This objective is achieved by combining an anti-ulceric antagonist of histamine H$_2$-receptors, preferably cimetidine; an antidepressant of Formula I in a racemic or optically active form, preferably nomiphenzene; and in some cases a spasmolytic agent, preferably 2-metoxycarbonyl-4-(beta-piperidinoethyl)benzophenone. The histamine antagonist is combined with the antidepressant in a ratio between 2:1 and 60:1. The antagonist-antidepressant combination may be combined with the spasmolytic agent in a ratio between 2.2:1 and 42.5:1.

The combination of histamine antagonist and racemic antidepressant according to the invention produces an unexpected and synergistic improvement in anti-ulcer activity in comparison with the independent administration of the antagonist cimetidine.

The use of the optically active [+] isomer of nomiphenzine provides a particularly active anti-ulcer composition, while the [−] isomer is inactive. For example, the anti-ulceric effect of cimetidine in a dose of 20 mg/kg in combination with [+] nomiphenzine in a dose of 1 mg/kg is equal to the anti-ulceric effect of 20 mg/kg cimetidine in combination with 2 mg/kg of racemic nomiphenzine. The [+] isomer is therefore twice as active as the racemic mixture, when comparing anti-ulcer properties.

Each administration of the composition of the invention, in a preferred embodiment, can be dosed as follows: from 50 to 400 mg of cimetidine, from 2.5 to 5 mg of [+] nomiphenzine, and (if desired) from 1 to 5 mg of the spasmolytic baralginketone. The total daily dosage of the composition is from 150 to 2400 mg of cimetidine, from 15 to 150 mg of [+] nomiphenzine, and (if desired) from 3 to 30 mg of baralginketone, in from 3 to 6 administrations.

The combination of the invention provides a number of advantages. The anti-ulceric activity of the composition is synergistically increased over that of cimetidine alone, so that smaller doses of cimetidine may be used and the serious toxicity and harmful side-effects associated with cimetidine are significantly reduced. The invention is useful as an anti-ulcer composition for prophylaxis and treatment of stomach and duodenum ulcers, including stress ulcers. Cimetidine alone is not effective as an inhibitor of ulcers caused by severe stress.

The combination of the invention is preferably dosed as a whole, through the administration of a finished pharmaceutical preparation made according to known methods. The active ingredients, or their pharmaceutically suitable salts, are combined with known excipients and carriers to form, for example, a convenient pill or capsule.

PREFERRED EMBODIMENTS

The invention is further described with reference to a number of examples which are illustrative only, and which do not serve to limit the scope of the disclosure and the accompanying claims.

EXAMPLE 1

Water Immersion Stress Ulcers

Pharmacological experiments were conducted on 385 white Vistar rats of both sexes, according to a slightly modified version of the method described in Takagu et al., *Chem. Pharm. Bull.*, Vol. 12, pp. 465–72 (1964). The results are set forth below in TABLES 1–4.

Approximately 18 hours prior to administration of the composition, the rats were submitted to a hunger regime with free access to water. The combination was then administered per os. Each rat was bound to a support on its back and was immersed in water thermoregulated at 23° C. Five hours later the animals were sacrificed and their stomachs examined.

TABLE 1 shows that a combination of 1 mg/kg cimetidine and 0.1 mg/kg racemic nomiphenzene produced an ulcer index of 31.6, while the untreated control produced an ulcer index of 47.6, for a suppression of 33.6%. A tenfold increase in dosage (10 mg/kg cimetidine and 1.0 mg/kg racemic nomiphenzene reinforced the anti-ulcer effect and produced a 51.6% suppression of the ulcer index. The strongest anti-ulcer effect in this series was achieved by a combination of 50 mg/kg cimetidine and 9 mg/kg racemic nomiphenzene, which produced an ulcer index of 0.73, compared to the control group index of 30; resulting in a suppression as high as 97.6%.

TABLE 2 shows that a combination of 20 mg/kg cimetidine, 1 mg/kg nomiphenzene, and 0.250 mg/kg baralginketone produced an ulcer index of 8.7 while the control produced an ulcer index of 53.3, for a suppression of 83.7%. This is almost as high as the suppression achieved by 20 mg/kg cimetidine and 3 mg/kg racemic nomophenzene. An increase in the nomiphenzene dose to 2 mg/kg results in a further increase in anti-ulcer effect. See TABLE 3.

In male rats, the control ulcer index of 58.2 decreases to as low as 2.5 with administration of the composition, for a suppression of 95.7%. According to the table, the strongest anti-ulcer effect in the series is shown by use of racemic nomiphenzene (76.3%) compared to cimetidine alone (52.9%).

The effect is even more pronounced in female rats. See TABLE 3. The ulcer index of 42.9 in the control group is reduced to 0.4 in treated animals, a suppression of 99%. This combination (20 mg/kg cimetidine, 2 mg/kg nomiphenzene, and 0.250 mg/kg baralginketone) therefore performs as well or better than the combination of TABLE 1 (50 mg/kg cimetidine and 9 mg/kg racemic nomiphenzene), yet less than half the amount of dangerously toxic cimetidine is needed. See TABLE 4.

If the racemic nomiphenzene of TABLES 1–3 is replaced with the optically active [+] isomer, the nomiphenzine dosage may be halved. The activity of 20 mg/kg cimetidine and 1 mg/kg [+] nomiphenzine is equivalent to 20 mg/kg cimetidine and 2 mg/kg racemic nomiphenzine.

EXAMPLE 2

Administration in Pill Form

A pharmaceutical pill is composed of the following ingredients:

| | |
|---|---|
| cimetidine | 0.1000 g |
| [+] nomiphenzene | 0.010 g |
| baralginketone | 0.002 g |
| wheat starch | 0.043 to 0.048 g |
| microcrystalic cellulose | 0.058 to 0.062 g |
| luviskol A64 | 0.003 to 0.0035 g |
| talc | 0.007 to 0.008 g |
| polyvinyl pyrolidone K25 | 0.005 to 0.006 g |
| magnesium stearate | 0.002 to 0.003 g |
| aerosil 200 | 0.002 to 0.004 g |
| varnish coating | 0.003 to 0.005 g |

EXAMPLE 3

Administration in Pill Form

Another pill is composed of the following ingredients:

| | |
|---|---|
| cimetidine | 0.100 g |
| [+] nomiphenzene | 0.010 g |
| wheat starch | 0.055 to 0.062 g |
| microcrystalic cellulose | 0.055 to 0.065 g |
| luviskol A64 | 0.002 to 0.004 g |
| talc | 0.007 to 0.008 g |
| polyvinyl pyrolidone K25 | 0.004 to 0.006 g |
| magnesium stearate | 0.002 to 0.003 g |
| aerosil 200 | 0.002 to 0.004 g |
| varnish coating | 0.003 to 0.005 g |

EXAMPLE 4

Administration in Capsule Form

A capsule is composed of the following:

| | |
|---|---|
| cimetidine | 0.100 g |
| [+] nomiphenzene | 0.010 g |
| wheat starch | 0.040 to 0.060 g |
| microcrystalic cellulose | 0.055 to 0.065 g |
| talc | 0.007 to 0.008 g |
| magnesium stearate | 0.002 to 0.003 g |
| aerosil 200 | 0.002 to 0.004 g |

EXAMPLE 5

Administration in Capsule Form

Another capsule is composed of the following:

| | |
|---|---|
| cimetidine | 0.100 g |
| [+] nomiphenzene | 0.010 g |
| baralginketone | 0.002 g |
| wheat starch | 0.040 to 0.060 g |
| microcrystalic cellulose | 0.055 to 0.065 g |
| talc | 0.007 to 0.008 g |
| magnesium stearate | 0.002 to 0.003 g |
| aerosil 200 | 0.002 to 0.004 g |

The ranges, as claimed, are established experimentally in using different quantities of several compounds of the groups I [histamine $H_2$ antagonist] and II [antidepressant]. These examples shown above reflect experiments with cimetidine as a representative of the compounds from group I [histamine $H_2$ antagonist] and nomiphenzene (racemic and [+] isomer) as representative of group II, the ratios being in the ranges of from 10:1 to 20:1.

The synergistic effect between ranitidine and (+)-nomiphenzine was established by carrying out experiments showing what suppression of the ulcer index was effected by aspirin and subchronic aspirin, according to the method of M. Muchakami, Japan as described in J. Pharmacology 32, p. 299–306, 1982.

In laboratory experiments, ranitidine was applied in doses 5 mg/kg while (+)-nomiphenzine 1 mg/kg combined or separately. The results obtained, as given in TABLE 5 below, show that the percentage of suppressing the ulcer index of ranitidine when applied independently is 23.75% while in combining it with (+)-nomiphenzine in the same dose, the percentage of the ulcer index is three times higher (70%). It is thus established that under these experimental conditions the antiulcer effect of the combination ranitidine (5 mg/kg) and (+)-nomiphenzine (1 mg/kg) is nearly 1.5 times higher compared to the effect in case of combination cimetidine (20 mg/kg) and (+)-nomiphenzine (1 mg/kg) this is 47.8% in spite of the fact that the ranitidine is applied in a 4 times lower dose.

The synergistic effect between ranitidine and (+)-nomiphenzine was confirmed also on the model of subchronic aspirin ulcer (TABLE 6). The percentage of suppressing the ulcer index of ranitidine, applied independently at a dose of 5 mg/kg, amounted to 26.4%, while in combining it with (+)-nomiphenzine (1 mg/kg) it is increasing nearly two times—44.13%.

As is seen in TABLE 6 the percentage of suppressing the ulcer index by the combination ranitidine and (+)-nomiphenzine is nearly equal of this of the combination cimetidine and (+)-nomiphenzine under the same experimental conditions though ranitidine is applied in a 4 times lower dose. This shows the improved effect obtained by the combination ranitidine, and experiments carried out show that the single therapeutic doses of the combination ranitidine and (+)-nomiphenzine are from 70 to 120 mg ranitidine and from 2.5 to 25 mg (+)-nomiphenzine. The total daily doses of the combination are from 160 to 480 mg ranitidine and from 15 to 150 mg (+)-nomiphenzine.

Although the invention is described and illustrated with reference to a plurality of embodiments thereof, it is to be expressly understood that it is in no way limited to the disclosure of such preferred embodiments but is capable of numerous modifications within the scope of the appended claims.

TABLE 1
INFLUENCE OF THE COMBINATION CIMETIDINE AND RACEMIC NOMIPHENZINE ON A MODEL OF AQUEOUS IMMERSION STRESS ULCERS

| Administered substance in dose - mg/kg p.o. | check ulcer index | Cimetidine ulcer index | % of suppressing of ulcer index | nomiphenzine ulcer index | % of suppressing of ulcer index | cimetidine and nomiphenzine ulcer index | % of suppressing of ulcer index |
|---|---|---|---|---|---|---|---|
| cimetidine 1 mg/kg and nomiphenzine 0,1 mg/kg | 47,6 | — | — | — | — | 31,6 | −33,6 |
| cimetidine 10 mg/kg nomiphenzine 1 mg/kg | 43,4 | 39,8 | −8,3 | 21,8 | −49,8 $p < 0,05$ | 21 | −51,6 $p < 0,05$ |
| cimetidine 20 mg/kg nomiphenzine 3 mg/kg | 30 | — | — | — | — | 3,5 | −88,3 $p < 0,001$ |
| cimetidine 50 mg/kg nomiphenzine 9 mg/kg | 30 | — | — | — | — | 0,73 | −97,6 $p < 0,001$ |

TABLE 2
INFLUENCE OF COMBINATION CIMETIDINE, NOMIPHENZINE RACEMATE AND BARALGINKETON ON A MODEL OF AQUEOUS IMMERSION STRESS ULCERS

| Administered substance mg/kg p.o. | Check U.I. | cimetidine U.I. | % of suppressing U.I. | nomiphenzine U.I. | % of suppressing U.I. | baralginketone U.I. | % of suppressing U.I. | cimetidine nomiphenzine, baralginketone U.I. | % of suppressing U.I. |
|---|---|---|---|---|---|---|---|---|---|
| cimetidine 20 mg/kg nomiphenzine 1 mg/kg baralginketone 0,25 mg/kg | 53,3 | — | — | — | — | — | — | 8,7 | −83,7 $p < 0,001$ |

TABLE 3
INFLUENCE OF COMBINATION CIMETIDINE, NOMIPHENZINE RACEMATE, BARALGINKETONE ON AN EXPERIMENTAL MODEL OF AQUEOUS IMMERSION ULCERS

| Administered substance dose mg/kg p.o. | check U.I. | cimetidine U.I. | % of pressing U.I. | nomiphenzine U.I. | % of suppressing U.I. | baralginketone U.I. | % of suppressing U.I. | cimetidine, nomiphenzine baralginketone U.I. | % of suppressing of U.I. |
|---|---|---|---|---|---|---|---|---|---|
| *male rats* | | | | | | | | | |
| cimetidine 20 mg/kg nomiphenzine 2 mg/kg baralginketone 0,25 mg/kg | 58,2 | 27,4 | −52,9 $p < 0,01$ | 13,8 | −76,3 $p < 0,001$ | 39,1 | −32,8 | 2,5 | −95,7 $p < 0,01$ |
| *female rats* | | | | | | | | | |
| cimetidine 20 mg/kg nomiphenzine 2 mg/kg baralginketone 0,25 mg/kg | 42,9 | 15 | −65 $p < 0,001$ | 19,5 | −54,5 $p < 0,01$ | 34,9 | −18,6 | 0,4 | −99 $p < 0,01$ |

Note:
U.I. ulcer index

TABLE 4
INFLUENCE OF CIMETIDINE AND + NOMIPHENZINE ON A MODEL OF AQUEOUS IMMERSION STRESS ULCERS

| CHECK (control) | −nomiphenzine | | +nomiphenzine | | cimetidine and + nomiphenzine | | cimetidine + and nomiphenzine resp. | |
|---|---|---|---|---|---|---|---|---|
| | 1 mg/kg | | 1 mg/kg | | 20 mg/kg | 1 mg/kg | 20 mg/kg | 2 mg/kg |
| | U.I. | % of suppressing U.I. | U.I. | % of suppressing U.I. | U.I. | % of suppressing U.I. | U.I. | % of suppressing U.I. |
| 56,95 (±11,4) | 50 (±17,1) | −13 | 16+ (±5,3) | −72 | 9+ (±5) | −84 | 6+ (±5,5) | −89 |

Note:
U.I. is ulcer index
+ presence of statistically important difference with view to the control group

TABLE 5

| Control | Doses | | |
|---|---|---|---|
| aspirin | ranitidine | ranitidine | (+)-nomiphenzine |
| 200 mg/kg | 5 mg/kg (+)-nomiphenzine 1 mg/kg | 5 mg/kg | 1 mg/kg |
| | suppression of ulcer index, % | suppression of ulcer index, % | suppression of ulcer index, % |
| | 70 | 23.75 | 24.7 |

TABLE 6
Influence of the combination of ranitidine and (+)-nomiphenzine on an aspirin subchronic ulcer model in rats

| Control aspirin nomi- | Doses | | | | |
|---|---|---|---|---|---|
| | cimetidine | ranitidine | cime-tidine | rani-tidine | (+)-phenzine |
| 100 mg/kg | 20 mg/kg (+)-nomiphenzine 1 mg/kg | 5 mg/kg (+)-nomiphenzine 1 mg/kg | 20 mg/kg | 5 mg/kg | 1 mg/kg |
| Suppression of the ulcer index in % | | | | | |
| 52.8 | 44.13 | 42.5 | 26.4 | 5.74 | |

We claim:

1. An anti-ulceric composition comprising
a histamine H₂ antagonist wherein the antagonist is a guanidine derivative selected from the group consisting of cimetidine or ranitidine and their pharmaceutically acceptable salts; and
at least one 4-phenyl-tetrahydroisoquinoline antidepressant of the formula:

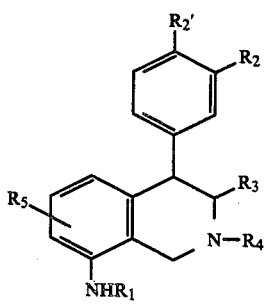

wherein $R_1$, $R_3$, and $R_4$ are each selected from the group consisting of hydrogen, a lower alkyl, and an aralkyl group; $R_2$ and $R'_2$ are each selected from the group consisting of hydrogen, a halogen atom, trifluormethyl, an alkyl, an alkoxy, and an aralkoxy group; and $R_5$ is selected from the group consisting of hydrogen, a halogen atom, a hydroxyl group, trifluormethyl, a nitro group, a lower alkyl, an alkoxy, and an aralkoxy group,
in a ratio of histamine antagonist to antidepressant of from 2:1 to 60:1.

2. An anti-ulceric composition comprising
a histamine antagonist selected from the group consisting of cimetidine or ranitidine and their pharmaceutically acceptable salts; and
at least one antidepressant selected from the group consisting of racemic and optically active 4-phenyltetrahydroisoquinolines of the formula:

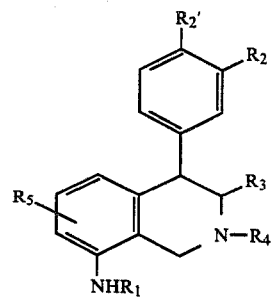

wherein $R_1$, $R_3$, and $R_4$ are each selected from the group consisting of hydrogen, a lower alkyl, and an aralkyl group; $R_2$ and $R'_2$ are each selected from the group consisting of hydrogen, a halogen atom, trifluormethyl, an alkyl, an alkoxy, and an aralkoxy group; and $R_5$ is selected from the group consisting of hydrogen, a halogen atom, a hydroxyl group, trifluormethyl, a nitro group, a lower alkyl, an alkoxy, and an aralkoxy group,
in a ratio of histamine antagonist to antidepressant of from 5:1 to 20:1.

3. An anti-ulceric as in claim 2, additionally comprising the spasmolytic agent 2-metoxycarbonyl-4-(beta-piperidinoethyl)benzophenone, with a ratio of antagonist and antidepressant, taken together, to spasmolytic agent of from 2.2:1 to 42.5:1.

4. A composition as in claim 3, wherein the antidepressant is selected from the group consisting of 4-phenyl-2-methyl-8-amino-1,2,3,4-tetrahydro-isoquinoline, its suitable salts, and its optical isomers.

5. A composition as in claim 3, wherein the antidepressant is the [+] isomer of 4-phenyl-2-methyl-8-amino-1,2,3,4-tetrahydroisoquinoline hydrogen maleate.

6. An anti-ulceric composition comprising
a histamine antagonist selected from the group consisting of [N-cyano-N'-methyl-N"]-2(4-methylimidazolyl)-methylthio[ethylguanidine] and its pharmaceutically acceptable salts;

the antidepressant 4-phenyl-2-methyl-8-amino-1,2,3,4-tetrahydro-isoquinoline hydrogen maleate as a [+] isomer, and the spasmolytic agent 2-metoxycarbonyl-4-(betapiperidinoethyl)benzophenone, wherein the ratio of antagonist to antidepressant to spasmolytic is 10:1:0.2.

7. An anti-ulceric composition comprising a histamine antagonist selected from the group consisting of [N-cyano-N'-methyl-N"]-2(4-methyl-imidazolyl)-methylthio[ethylguanidine] and its pharmaceutically acceptable salts and the antidepressant 4-phenyl-2-methyl-8-amino-1,2,3,4-tetrahydro-isoquinoline hydrogen maleate as a [+] isomer, wherein the ratio of antagonist to antidepressant is 10:0.5.

8. An anti-ulceric composition comprising a histamine $H_2$ antagonist wherein the antagonist is a guanidine derivative selected from the group consisting of cimetidine or ranitidine and their pharmaceutically acceptable salts;

the antidepressant racemic nomiphenzene, and the spasmolytic agent baralginketone wherein the ratio of antagonist to antidepressant to spasmolytic is 10:1:0.2.

9. An anti-ulceric composition comprising a histamine $H_2$ antagonist wherein the antagonist is a guanidine derivative selected from the group consisting of cimetidine or ranitidine and their pharmaceutically acceptable salts and the antidepressant racemic nomiphenzene, and wherein the ratio of antagonist to antidepressant is 10:0.5.

* * * * *